(12) United States Patent
Fuss et al.

(10) Patent No.: US 6,613,090 B2
(45) Date of Patent: Sep. 2, 2003

(54) INTERVERTEBRAL IMPLANT

(75) Inventors: Franz Konstantin Fuss, Wiener Neustadt (AT); Ronald J. Sabitzer, Wien (AT); Stephan Eckhof, Tuttlingen (DE)

(73) Assignee: Aesculap AG & Co. KG, Tuttlingen (DE)

( * ) Notice: Subject to any disclaimer, the term of this patent is extended or adjusted under 35 U.S.C. 154(b) by 78 days.

(21) Appl. No.: 09/917,196

(22) Filed: Jul. 27, 2001

(65) Prior Publication Data

US 2002/0022886 A1 Feb. 21, 2002

Related U.S. Application Data

(63) Continuation of application No. PCT/EP00/00624, filed on Jan. 27, 2000.

(30) Foreign Application Priority Data

Jan. 30, 1999 (DE) .......................... 199 03 764

(51) Int. Cl.⁷ ................................. A61F 2/44
(52) U.S. Cl. ..................................... 623/17.11
(58) Field of Search ................... 623/17.11–17.16; 606/60, 61, 62, 71, 72, 73

(56) References Cited

U.S. PATENT DOCUMENTS

| 4,904,261 | A | * | 2/1990 | Dove et al. | 623/17.11 |
| 4,917,704 | A | * | 4/1990 | Frey et al. | 623/17.11 |
| 5,702,449 | A | * | 12/1997 | McKay | 623/17.11 |
| 5,861,041 | A | * | 1/1999 | Tienboon | 623/17 |
| 6,111,164 | A | * | 8/2000 | Rainey et al. | 623/16 |
| 6,143,033 | A | * | 11/2000 | Paul et al. | 623/17.11 |
| 6,454,805 | B1 | * | 9/2002 | Baccelli et al. | 623/17.11 |
| 6,482,233 | B1 | * | 11/2002 | Aebi et al. | 623/17.11 |
| 2002/0161445 | A1 | * | 10/2002 | Crozet | 623/17.11 |

FOREIGN PATENT DOCUMENTS

| DE | 3637314 A1 | * | 5/1988 | 623/17.11 |
| FR | 2736537 A1 | * | 1/1997 | 623/17.11 |

* cited by examiner

Primary Examiner—Corrine McDermott
Assistant Examiner—Alvin Stewart
(74) Attorney, Agent, or Firm—Barry R. Lipsitz; Douglas M. McAllister

(57) ABSTRACT

In an intervertebral implant having an upper and a lower supporting surface for abutment with adjacent vertebral bodies, having a concave dorsal longitudinal side, a ventral longitudinal side lying opposite the latter, having a rounded contour at the two end faces connecting the longitudinal sides and having at least one hole extending through the implant from the upper to the lower supporting surface, in order to facilitate the introduction of bone material after insertion of the intervertebral implant into an intervertebral space it is proposed that in the region of the middle portion of the ventral longitudinal side at least one introduction channel for bone material, which extends through the implant, exits from the implant.

18 Claims, 5 Drawing Sheets

Figure 1:
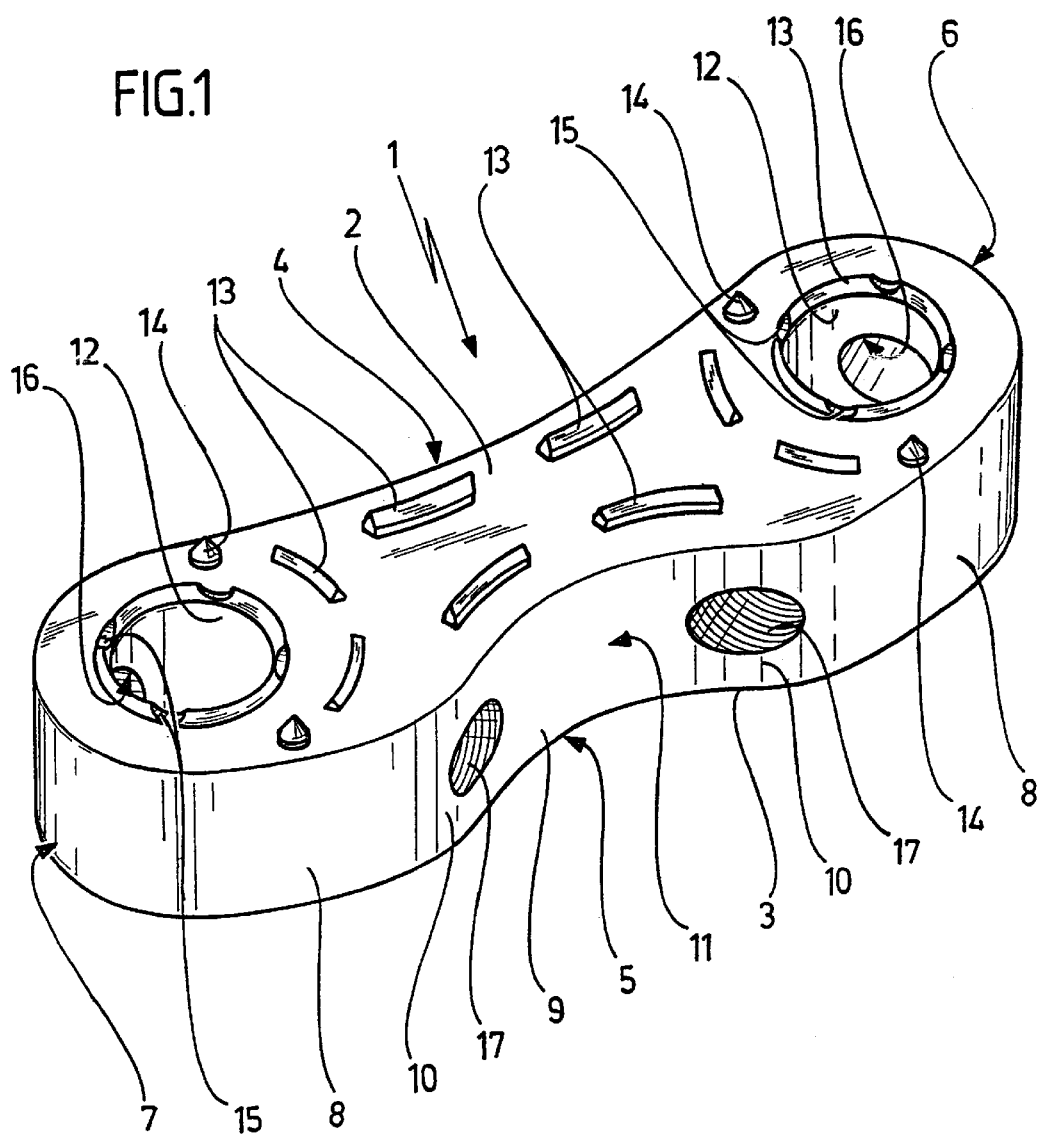

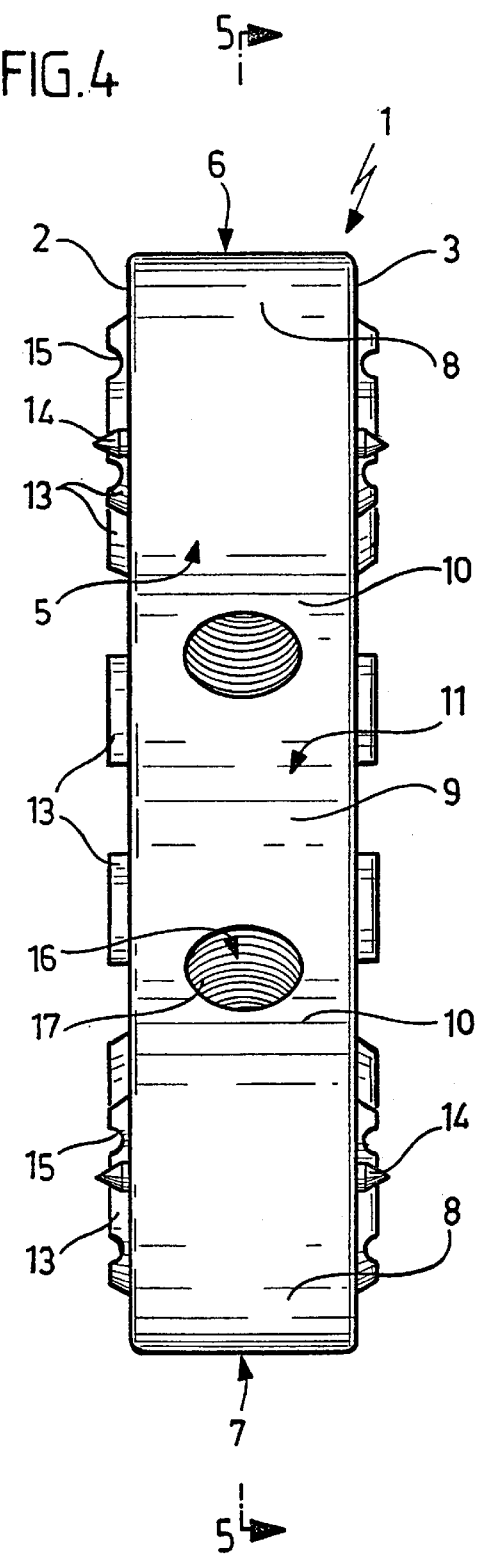
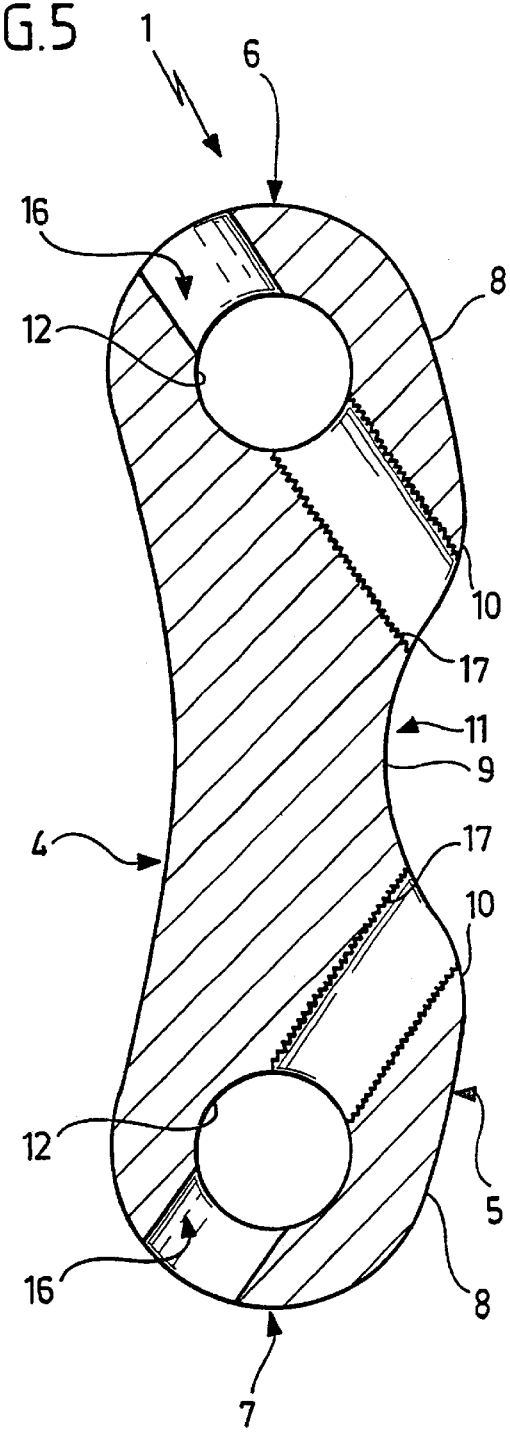

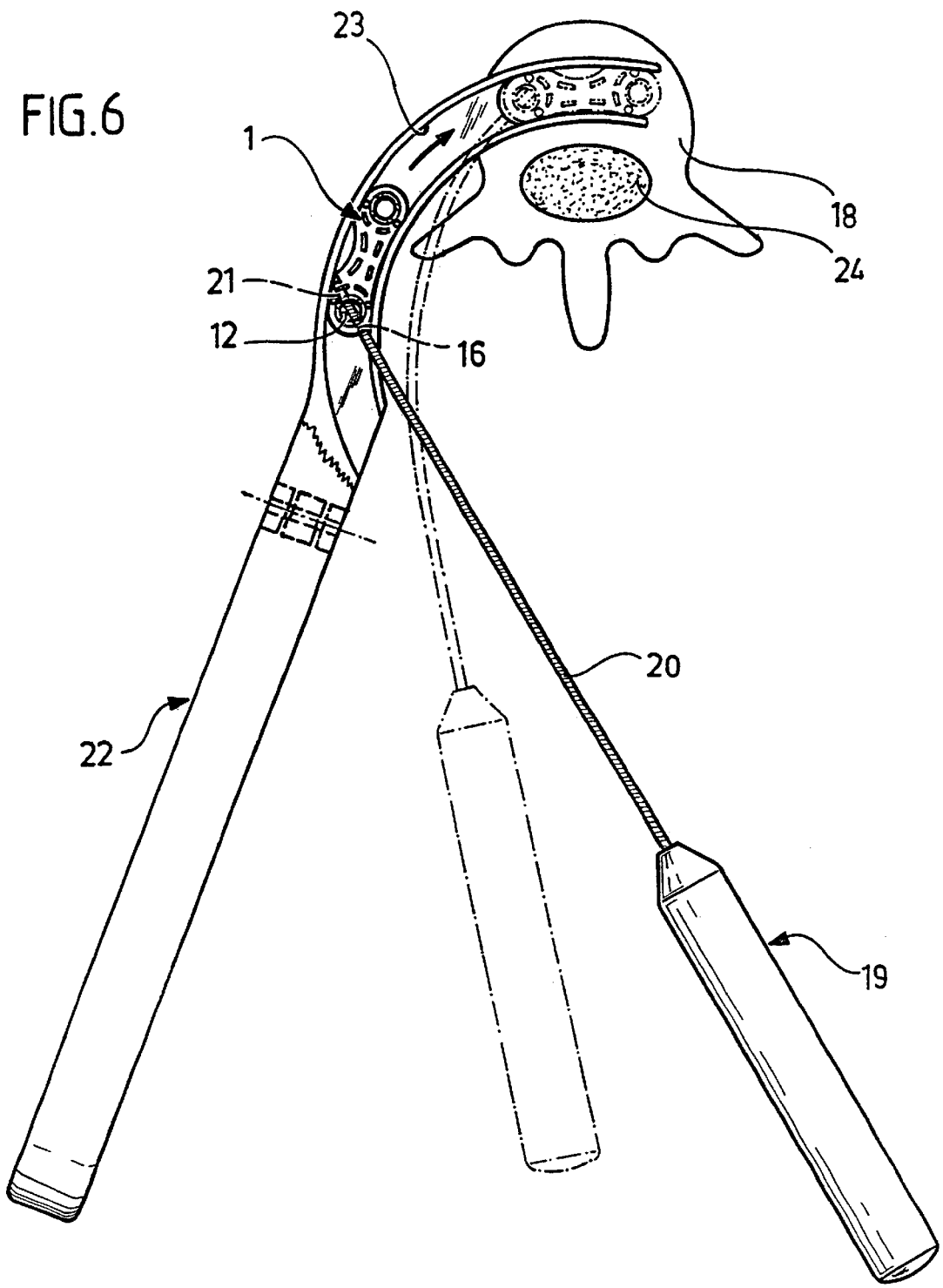

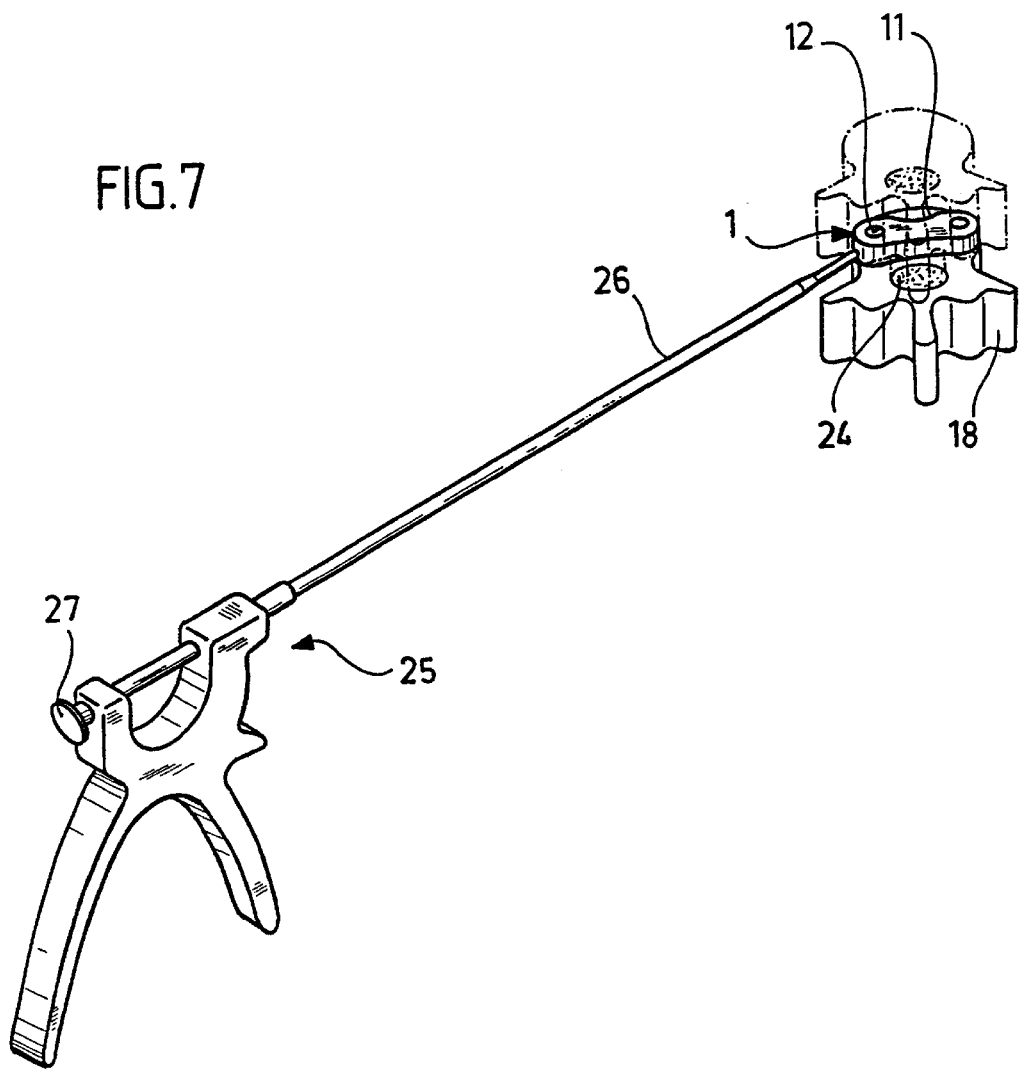

INTERVERTEBRAL IMPLANT

This application is a continuation of international application number PCT/EP00/00624 filed on Jan. 27, 2000.

The invention relates to an intervertebral implant having an upper and a lower supporting surface for abutment with adjacent vertebral bodies, having a concave dorsal longitudinal side, a ventral longitudinal side lying opposite the latter, having a rounded contour at the two end faces connecting the longitudinal sides and having at least one hole extending through the implant from the upper to the lower supporting surface.

Such an intervertebral implant is known, for example, from DE 297 20 022 U1. It is used, after removal of a disk, partially to fill the intervertebral space between two adjacent vertebral bodies and thereby support the adjacent vertebral bodies against one another. Besides the support function said implants are also intended to enable a bony fusion of adjacent vertebral bodies, which is why they only partially fill the intervertebral space; in the construction known from DE 297 20 022 U1 the implant is formed from relatively narrow side walls, which with their top and their bottom edge form only a small supporting surface for the adjacent vertebral bodies. When an intervertebral implant is used, which substantially takes the form of a solid body and only has holes for receiving the bone material, it is frequently difficult to introduce the bone material into said holes and into remaining free spaces of the intervertebral space.

The object of the invention is to design an intervertebral implant of the type described in such a way that even after insertion of the intervertebral implant into the intervertebral space it is still easily possible to introduce bone material into regions of the intervertebral space not occupied by the implant.

In an intervertebral implant of the type described initially, said object is achieved according to the invention in that in the region of the middle portion of the ventral longitudinal side at least one introduction channel for bone material, which extends through the implant, exits from the implant. The provision in the implant of such an introduction channel, which exits from the implant in the middle region of the ventral longitudinal side, makes it possible for bone material to be introduced through the inserted implant into the intervertebral space and disposed in the region of the intervertebral space ventrally adjoining the inserted implant, thereby ensuring that bony growth sets in immediately adjacent to the inserted implant and the implant is therefore fixed in its inserted position between the adjacent vertebral bodies.

It is advantageous if the introduction channel enters the implant in the part of an end face adjoining the dorsal longitudinal side. By said means bone material may be introduced dorsolaterally into the implant and may pass from the introduction side through the implant to the ventral side of the intervertebral space; in said manner access is therefore made considerably easier.

It is particularly advantageous if the introduction channel crosses a hole, which extends through the implant. Thus, the introduction channel may also be used to introduce bone material into the hole.

In a particularly preferred embodiment of the invention it is provided that the introduction channel at its ventral end has fastening elements for an instrument inserted into the introduction channel. The introduction channel therefore has a dual function, on the one hand it is namely used to fill the intervertebral space with bone material and on the other hand it may receive an instrument, which is used e.g. to manipulate the intervertebral implant and insert the latter into the intervertebral space. By means of the fastening elements the instrument may be firmly connected to the implant so that the surgeon may delicately guide the implant during insertion.

As a fastening element a bayonet catch, for example, might be used, it is particularly advantageous if the fastening element is formed by an internal thread.

The introduction channel preferably extends in a plane, which is disposed substantially parallel to the supporting surfaces.

In said case, the introduction channel may be inclined between 30° and 80° relative to a longitudinal axis of the implant in a plane extending substantially parallel to the supporting surfaces.

In a preferred embodiment, two introduction channels enter the implant from different end faces of the latter so that the introduction of bone material and/or the manipulation of the implant may be effected by inserting a manipulating instrument from the direction of both end faces.

It is particularly advantageous if the implant is constructed symmetrically relative to a centre plane perpendicular to the supporting surfaces and to the longitudinal sides, thereby allowing the implant to be inserted in two orientations.

In a preferred embodiment it is provided that two holes are disposed at the two ends of the implant adjacent to the end face of the latter.

In particular, the holes may have a circular cross section.

It is advantageous if the supporting surfaces are inclined, e.g. at an angle of between 0° and 15°, relative to one another.

It may further be provided that the supporting surfaces carry projections, which assist the fixing to the adjacent vertebral bodies.

Said projections may be, for example, spike-shaped points or ribs.

It is particularly advantageous when the projections in the form of ribs extend along the edges of the holes. The holes are therefore surrounded by a rib-shaped collar, which may additionally comprise notches for improved connection to the adjacent vertebral bodies.

In another embodiment it is provided that the projections are microprojections, which are formed by a rough surface structure of the supporting surfaces. For said purpose, the supporting surfaces may be provided e.g. with a coating, which gives rise to a roughened surface structure comprising micropores.

Figure 2:
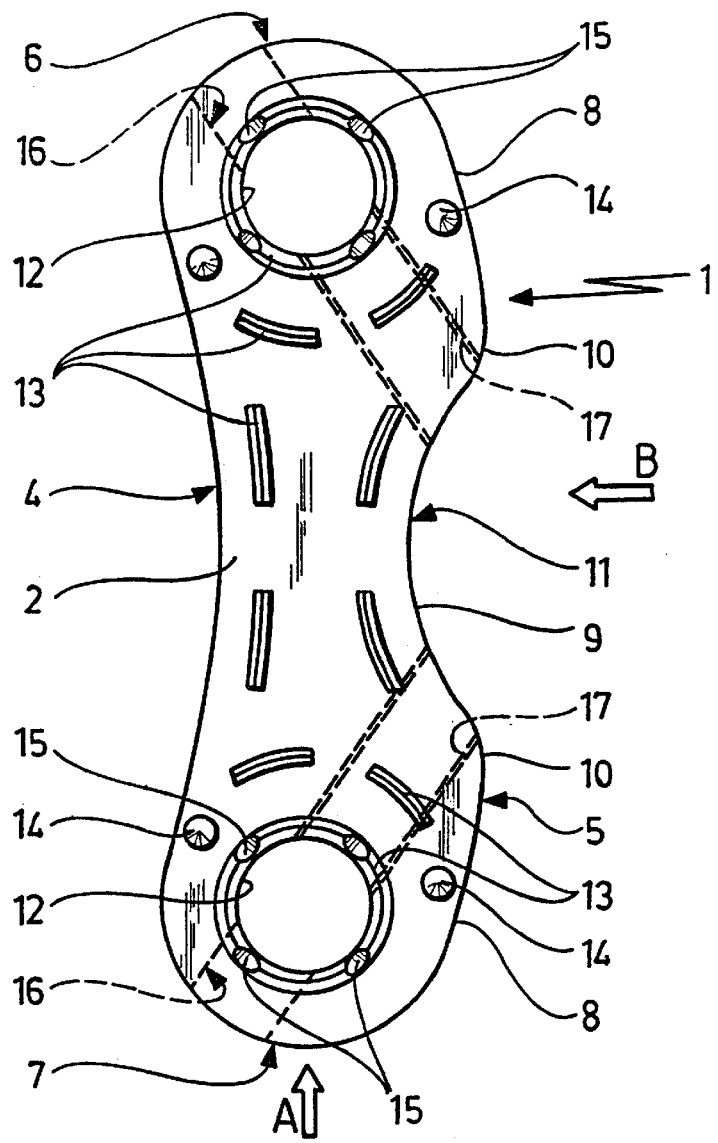
Figure 3:
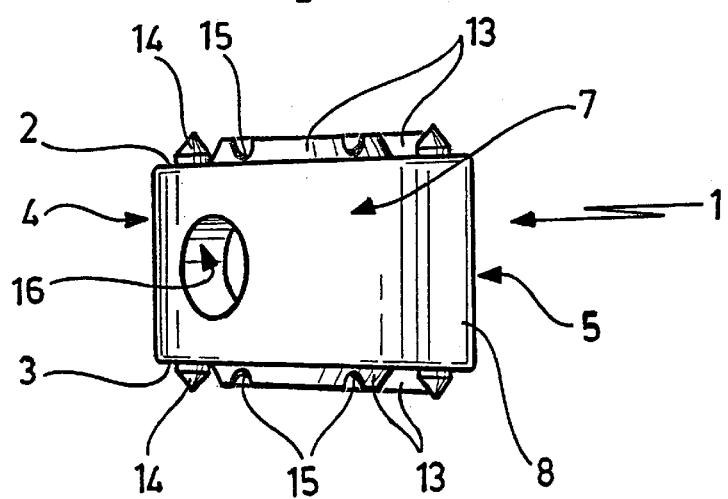

There now follows a detailed description of preferred embodiments of the invention with reference to the drawings. The drawings show:

FIG. 1: a perspective view of an intervertebral implant;
FIG. 2: a plan view of the implant of FIG. 1;
FIG. 3: a side view of the implant of FIG. 1 in the direction of the arrow A in FIG. 2;
FIG. 4: a side view of the implant of FIG. 1 in the direction of the arrow B in FIG. 2;
FIG. 5: a sectional view along line 5—5 in FIG. 4;
FIG. 6: a view of the process of insertion of the implant of FIGS. 1 to 3 with the aid of an insertion instrument and
FIG. 7: a view of the process of introducing bone material through the inserted implant by means of a filling instrument.

The intervertebral implant 1 illustrated in FIGS. 1 to 5 is of a plate-shaped design and comprises a flat upper supporting surface 2 and a flat lower supporting surface 3. The intervertebral implant 1 is laterally delimited by a vertical lateral surface, which is subdivided into a dorsal longitudinal side 4, a ventral longitudinal side 5 lying opposite the latter, and two end faces 6, 7 connecting said longitudinal sides.

The dorsal longitudinal side 4 is of a slightly concave construction and extends in a substantially uniform arc over the greatest part of the length of the intervertebral implant 1, wherein the radius of said arc is between 30 mm and 50 mm.

The two ends of the dorsal longitudinal side 4 are adjoined by the end faces 6, 7 with an arc-shaped contour, which each extend substantially over a semicircle and which merge continuously and without a bend into the ventral longitudinal side 5.

The ventral longitudinal side 5 is subdivided into two outer-lying side portions 8, which continuously and without bends adjoin the end faces 6, 7 and extend substantially parallel to the opposite parts of the dorsal longitudinal side 4, and into a middle portion 9, which is disposed between the two side portions 8, has a concave, arc-shaped contour and continues via convex arc-shaped intermediate portions 10 into the side portions 8. Here too, all transitions are continuous and without bends, wherein the radius of the concave middle portion 9 is, for example, between 5 mm and 15 mm.

Thus, the intervertebral implant 1 has an elongate, on the whole curved shape with a middle portion 9 forming a set-back recess 11, i.e. the intervertebral implant 1 is wider at its ends than in its middle (FIG. 2).

Holes 12, which are circular in cross section and have a diameter between 4 mm and 8 mm, extends through the intervertebral implant 1 concentrically with the arc-shaped end faces 6 and 7.

The upper supporting surface 2 and the lower supporting surface 3 are slightly inclined, e.g. at an angle of between 0° and 15° (FIG. 3), relative to one another so that the distance of the upper supporting surface 2 from the lower supporting surface 3 is smaller at the dorsal longitudinal side 4 than at the ventral longitudinal side 5.

The, as such, flat supporting surfaces 2 and 3 carry projections in the form of ribs 13 and spike-shaped points 14, wherein said ribs 13 extend partially along the edges of the holes 12 so that the holes 12 are surrounded in a collar-shaped manner by the ribs 13. Indentations 15 may be situated in the ribs 13 and subdivide the ribs 13 into individual portions.

Both holes 12 are diametrically crossed in each case by an introduction channel 16, which enters the intervertebral implant 1 at an end face 6 and/or 7 and exits from the latter in the region of the concave middle portion 9. The introduction channels extend in a plane, which is disposed between the upper supporting surface 2 and the lower supporting surface 3 and is positioned substantially parallel to said supporting surfaces, wherein relative to a longitudinal axis of the intervertebral implant 1 defined e.g. by the centres of the two holes 12 the introduction channels 16 form an angle between 20° and 120°.

In the entry region, i.e. at their front end, the introduction channels 16 have a smooth inner wall and at the exit end, i.e. at their recess-side end, they are provided with an internal thread 17.

The intervertebral implant 1 is preferably made of a bio-compatible metal, e.g. titanium or a titanium alloy, or of plastics material.

To insert the described intervertebral implant 1 into the intervertebral space, i.e. into the gap between adjacent vertebral bodies 18, the intervertebral implant 1 is connected to an insertion instrument 19, which comprises e.g. a flexible shank 20 having an external thread 21 on its end. Said shank 20 is inserted into an introduction channel 16 and screwed by means of its external thread 21 into the internal thread 17 of said channel so that the intervertebral implant 1 and the insertion instrument 19 form a unit.

Along a guide instrument 22, which is introduced dorsolaterally into the body and positioned with its free end in the intervertebral space, the intervertebral implant 1 is fed forward along the guideway 23 of the guide instrument 22 with the aid of the insertion instrument 19 until it is positioned with the dorsal longitudinal side 4 closely adjacent to the vertebral channel 24 of the vertebral body 18. As soon as said position is reached, the guide instrument 22 may be withdrawn from the body, the shank 20 of the guide instrument 22 is screwed out of the internal thread 17 and then the insertion instrument 19 may also be withdrawn from the body (FIG. 4).

In the inserted state, the intervertebral implant 1 is situated closely adjacent to the vertebral channel 24 and covers only part of the area of the intervertebral space between adjacent vertebral bodies 18.

After the intervertebral implant 1 has been inserted in the described manner, a filling instrument 25 having an elongate, thin filling tube 26 is introduced likewise dorsolaterally into the body and inserted into the introduction channel 16 (FIG. 7). By means of a suitable apparatus, e.g. by means of a plunger 27, bone material is introduced through the filling tube 26, out of the filling tube 26 and through the introduction channel 16 into the body and in said case initially fills the set-back recess 11 and the adjoining region of the intervertebral space, wherein said instrument may moreover be used also to fill the respective hole 12, through which the introduction channel 16 passes.

The introduced bone material compacts and forms, both in the hole 12 and also in particular in the set-back recess 11, a bony bridge between adjacent vertebral bodies 18, which is connected to the external contour of the intervertebral implant 1 and therefore locks the intervertebral implant 1 against any displacement in the intervertebral space.

The introduction channel 16 therefore performs a dual function, firstly as a receiver for the insertion instrument 19 and secondly as a supply route for bone material. Said introduction channel 16, because of its obliquely extending orientation, extends over a great length in the intervertebral implant 1 and therefore over a great length provides stable guidance especially for the insertion instrument 19, with the result that via the insertion instrument 19 optionally even greater forces may be exerted on the intervertebral implant 1 without any risk of damaging the intervertebral implant 1 or the shank 20 of the insertion instrument 19.

Furthermore, via the introduction channel 16 a supply of the bone material may be effected in the interior of the hole 12 and also in the interior of the set-back recess 11, wherein the growing of bone material through the introduction channel leads to a further connection and fixing of the intervertebral implant 1 in the intervertebral space.

What is claimed is:
1. An intervertebral implant comprising:
an upper and a lower supporting surface for abutment with adjacent vertebral bodies,
a concave dorsal longitudinal side,
a ventral longitudinal side lying opposite said dorsal longitudinal side, said ventral longitudinal side having a rounded contour at respective end faces connecting said longitudinal sides,
at least one introduction channel for bone material extending through the implant, said channel entering the implant in a portion of one of said end faces adjoining the dorsal longitudinal side and exiting from the implant in a portion of a middle region of the ventral longitudinal side, and fastening elements at the ventral end of said channel for an instrument to be inserted into said channel, wherein the introduction channel is inclined between 30° and 80° relative to a longitudinal axis of the implant in a plane extending substantially parallel to said upper and lower supporting surfaces.

2. An implant according to claim 1, wherein the introduction channel crosses a hole which extends through the implant.

3. An implant according to claim 2, wherein the fastening elements comprise internal threads.

4. An implant according to claim 1, wherein side portions of said ventral longitudinal side, which adjoin said middle region, extend substantially parallel to the dorsal longitudinal side.

5. An implant according to claim 1, wherein the supporting surfaces are inclined relative to one another.

6. An implant according to claim 1, wherein the introduction channel extends in a plane, which is disposed substantially parallel to the supporting surfaces.

7. An implant according to claim 1, wherein two introduction channels run from different end faces of the implant into a set-back recess of said middle region.

8. An implant according to claim 2, wherein the implant is constructed symmetrically relative to a center plane perpendicular to the supporting surfaces and to the longitudinal sides.

9. An implant according to claim 1, wherein the supporting surfaces carry projections.

10. An implant according to claim 9, wherein the projections are spike-shaped points.

11. An implant according to claim 9, wherein the projections are ribs.

12. An implant according to claim 11, wherein:

the introduction channel crosses a hole which extends through the implant; and the projections in the form of ribs extend along the edges of said hole.

13. An implant according to claim 1, wherein the ventral longitudinal side has a set-back recess in aid middle region for receiving bone material.

14. An implant according to claim 13, wherein the recess extends over the entire height of the implant.

15. An implant according to claim 13, wherein the recess is formed by a concave middle portion of the ventral longitudinal side, which middle portion has an arc-shaped contour.

16. An implant according to claim 15, wherein side portions of the ventral longitudinal side, which adjoin the middle portion, run in an arc-shaped manner and continuously into the middle portion.

17. An intervertebral implant comprising:

an upper and a lower supporting surface for abutment with adjacent vertebral bodies, a concave dorsal longitudinal side, a ventral longitudinal side lying opposite said dorsal longitudinal side, said ventral longitudinal side having a rounded contour at respective end faces connecting said longitudinal sides, and first and second introduction channels for bone material extending through the implant, each channel entering the implant in a portion of a respective one of said end faces adjoining the dorsal longitudinal side and exiting from the implant in a portion of a middle region of the ventral longitudinal side, wherein:

the introduction channels are inclined between 30° and 80° relative to a longitudinal axis of the implant in a plane extending substantially parallel to said upper and lower supporting surfaces, and the introduction channels each cross a respective hole extending through the implant adjacent the respective end face thereof.

18. An implant according to claim 17, wherein the holes have a circular cross section.

\* \* \* \* \*

UNITED STATES PATENT AND TRADEMARK OFFICE
CERTIFICATE OF CORRECTION

PATENT NO. : 6,613,090 B2
DATED : September 2, 2003
INVENTOR(S) : Fuss et al.

It is certified that error appears in the above-identified patent and that said Letters Patent is hereby corrected as shown below:

Column 5,
Line 14, change "2" to -- 1 --.
Line 28, change "2" to -- 1 --.

Column 6,
Line 4, "aid" should be corrected to read -- said --.

Signed and Sealed this

Twenty-third Day of December, 2003

JAMES E. ROGAN
*Director of the United States Patent and Trademark Office*